United States Patent [19]

Hilleman

[11] 4,371,336
[45] Feb. 1, 1983

[54] ORTHODONTIC POSITIONER

[76] Inventor: Terry B. Hilleman, 621 SW. 74th Ter., Plantation, Fla. 33317

[21] Appl. No.: 229,560

[22] Filed: Jan. 29, 1981

[51] Int. Cl.³ .............................................. A61C 7/00
[52] U.S. Cl. ...................................................... 433/6
[58] Field of Search ........................................... 433/6

[56] References Cited

U.S. PATENT DOCUMENTS 4,073,061  2/1978  Bergersen ............................... 433/6

Primary Examiner—Robert Peshock
Attorney, Agent, or Firm—Eugene F. Malin

[57] ABSTRACT

A trim tooth positioner is constructed to cover only the incisal edges and cusps of the teeth themselves. The result is that the majority of the bulk covering the teeth and gums is eliminated. This significantly increases patient comfort and greatly overcomes the major disadvantage of positioners, that is, poor patient cooperation. The performance is equal or superior to that of other positioner designs in that enhanced cooperation far outweighs any advantage offered by bulk.

3 Claims, 6 Drawing Figures

ORTHODONTIC POSITIONER

BACKGROUND OF THE INVENTION

Upon removal of fixed appliances, many orthodontists prefer to place a tooth-positioning device that is made from plaster casts of the teeth at the end of treatment. The teeth in the cast are cut out and rearranged slightly in wax to the most ideal arrangement possible. A custom-made tooth positioner is flasked of rubber, silicone, vinyl, urethane, acrylic, or similar resilient material to exactly fit the teeth in this ideal arrangement. The positioner is placed before the bone sets around the teeth that have been moved by the fixed appliance. The patients wear the positioner to bed at night and clench into the positioner for four hours a day while the bone forms for an eight-week period, as an example of use. The positioner acts as a cast on a broken arm in that the teeth are held in the desired position and, moreover, it guides the teeth to the most ideal place by the resilient material actively moving each tooth as the teeth are clenched during the four-hour daytime wear period. The amount of movement is more or less limited by the mobility of each tooth in its periodontal membrane space at the time of placement. Many orthodontists take impressions with the fixed appliances still in place and remove them when the construction of the custom-made positioner is completed. Another alternative is to use an off-the-shelf stock preformed positioner to act as an intermediate form of retention until the custom-made one is ready.

The major disadvantage to this ideal approach is poor patient cooperation. Any removeable retention appliance has to be in use in the patients mouth if it is going to be successful. Positioners in their present day design are not very comfortable. Their excess bulk makes patients gag, choke, salavate excessively, and many patients experience breathing difficulties which are only partially helped by air holes. The result is that many patients do not wear positioners as prescribed and teeth are not retained well, let alone improved in position. When the orthodontist sees the completed result go back towards the original situation before treatment started, he and the patient are very unhappy and the positioner is blamed for failure. Most orthodontists do not use them because of failure due to lack of patient cooperation.

Present-day designs not only completely cover all exposed surfaces of the teeth but a significant amount of the gum tissue (gingiva) and underlying bone supporting the teeth. The design of the tooth positioner such as described in the original article by H. B. Kesling and as shown in U.S. Pat. Nos. 2,467,432 and 2,531,222, see FIG. 25, covers nearly three times the amount of the supporting gingiva and underlying bone as the labial and buccal surfaces of the teeth in the immediate area.

SUMMARY OF THE INVENTION

A new and improved orthodontic tooth positioner covers the occlusal and incisal one third of all of the upper teeth and the occlusal and incisal one third of all the lower teeth. The top upper edges and the bottom lower edges of the positioner are sized and positioned to lay adjacent to the middle portion of the teeth and not to touch in any manner the gum tissue. The tooth positioner is a one piece article. This new positioner is less bulky than prior devices. The size, bulk, shape and weight of this positioner provides a prostetic device that elicits a user's cooperation for continued use. The distance between the lower and upper teeth impressions in the positioner is 2 to 3 millimeters.

The impressions in the top and bottom of the positioner are tooth impressions of the user. The tooth impressions are positioned in the desired or ideal position or arrangement in order to move the teeth of a user to a preferred new proper position. The tooth positioner is made of plastic, such as thermal methylmethacrylate. The positioner is made of a resilient material that will exert a constant pressure on the teeth to move them to the desired position and hold them there.

With using the proper material, covering the incisal edges on anteriors and cusps on posteriors is all that is required with the daily exercising and nighttime wear. The result is that with only a fraction of the bulk covering the teeth, patient comfort is greatly enhanced and cooperation is greatly improved. The new design positioner is more comfortable and far less bulky. Over half of the bulk is eliminated with the new invention.

It is an object of this invention to size and shape the tooth positioner to the cutting and grinding tips of teeth; that is, the incisal edges on anteriors and cusps on posteriors, for daily excersizing and nighttime wear.

It is another object of this invention to provide a tooth positioner that covers the labial and buccal surfaces of the teeth without contacting or covering the gum tissue, thereby substantially reducing the bulk.

It is another object of this invention to provide a tooth positioner with little bulk covering the teeth to provide a significant increase in patient comfort which greatly enhances and improves patient cooperation.

It is another object of this invention to provide a tooth positioner with performance equal or superior to that of other positioner designs in that enhanced cooperation far outweighs any advantage afforded by bulk.

In accordance with these and other objects which will be apparent hereinafter, the instant invention will now be described with particular reference to the accompanying drawings.

REFERENCE TO THE DRAWINGS

DESCRIPTION OF A PREFERRED EMBODIMENT

Figure 6:
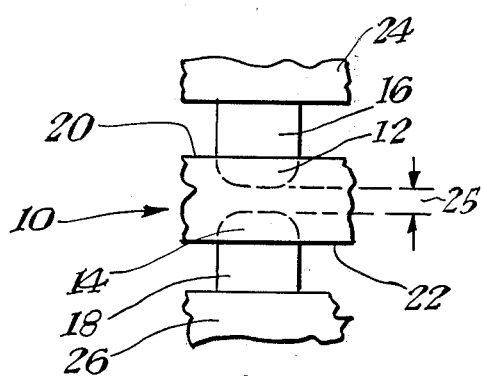
FIG. 6 is an enlarged illustration showing a portion of a user's teeth and gums in a positioner.

Referring now to the drawings FIGS. 1 through 6 the orthodontic tooth positioner 10 covering the entire occlusal and incisal one third illustrated by numerals 12 and 14 as specifically shown in FIG. 6. The upper portion 16 of the upper teeth and the lower portion 18 of the lower teeth are not covered. The tooth positioner 10 is a one piece article. The one piece molded tooth positioner 10 has a top edges 20 and bottom edges 22 sized and shaped to not cover or touch gum tissue 24 and 26. The portions of the teeth 16 and 18 are left exposed and uncovered. The tooth positioner is therefore less bulky, smaller in size and of less weight than prior positioners. The size and shape provides a prostetic device that elicits a user's cooperation for continued use and thereby providing a better end result. The new and improved teeth positioner is shaped and sized as shown in FIGS. 1, 2, 3, 4, and 5 so that the cusp-fossa relationships are re-enforced and centric occlusion is maintained.

The FIGS. 1 through 5 show the new design positioner engaging only the contacting edges of the teeth; that is, the occlusal and incisal one third of the teeth. The distance between the impressions 30 in the top of the molded positioner and the impressions 32 in the bottom of the positioner is the distance of approximately two millimeters. The sides of the positioner adjacent the tooth impressions 30 and 32 deliver the lateral pressure. The approximate two millimeters of acrylic separating the upper teeth from the lower to provide enough bulk for strength to resist breakage. The teeth are arranged in the most ideal occlussion in a set-up mounted on an articulator. The positioner is formed from thermal acrylic or any other suitable resilient material to the design shown in FIGS. 1 through 5.

Figure 3:
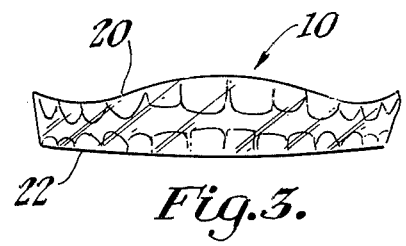
FIG. 3 is a front view of the orthodontic positioner.
Figure 4:
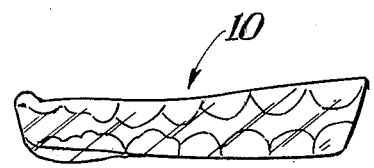
FIG. 4 is a side view of the orthodontic positioner.
Figure 2:
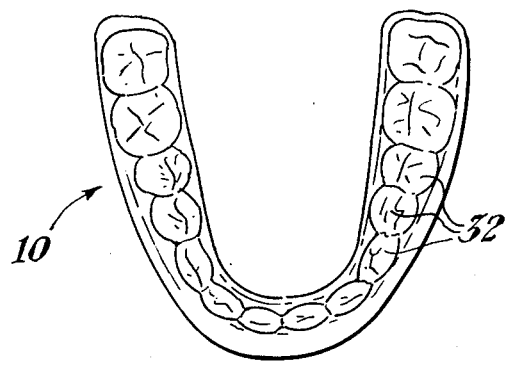
FIG. 2 is a bottom view of the orthodontic positioner.
Figure 5:
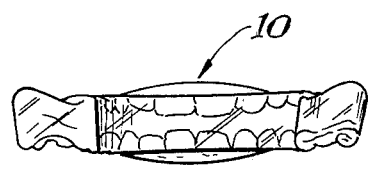
FIG. 5 is a rear view of the orthodontic positioner.
Figure 1:
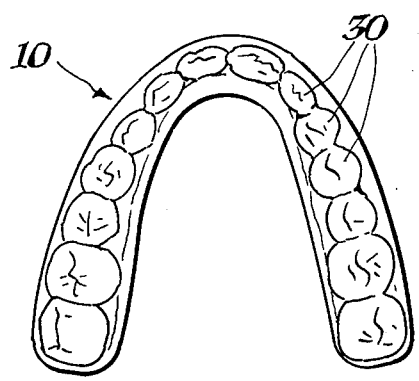
FIG. 1 is a top plan view of the orthodontic positioner.

FIG. 1 reveals that the new design positioner engages only the contacting edges of the teeth; namely the occlusal surfaces and incisal or cusp edges. From these surfaces for a distance of two to three millimeters, the incisal and cusp areas of the labial, lingual, and buccal surfaces are engaged in the model set-up to become part of the appliance and deliver the lateral pressure.

The performance is equal or superior to that of other positioner designs in that enhanced cooperation far outweighs any advantage afforded by bulk. Cusp-fossa relationships are re-enforced and centric occlusion is maintained throughout the retention and/or post-treatment growth period with nighttime wear, assuming proper fixed appliance therapy before positioner use.

The material most ideal for fabrication is thermally-activated Methyl Methacrylate. It is conceivable that good results could be obtained with rubber, silicone, vinyl, urethane, or any resilient material used in present day positioners but the thermal acrylic offers the greatest range on deformation when warmed, greatest rigidity when at room temperature, and ideal resiliency when at mouth temperature. It does not discolor like the vinyl and silicone and yet does not taste bad as the rubber does.

It is recommended that the patient warm it in hot tap water before use to gain maximum stretch. It should be at least warmed to mouth temperature before clenching in order to approach the elasticity of rubber.

It may be constructed with all three popular methods of articulation. The modified articulator with two millimeter bite opening is one alternative, another is the hinge-axis articulation from headfilm guidelines, and the third is the method using articulator setups that analyze centric and eccentric jaw movements.

The positioner functions optimally when constructed to fit over a cemented lower lateral to lateral, cuspid to cuspid, or bicuspid to bicuspid fixed retainer.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An improved tooth positioner utilizing tooth contacting edges for actively moving individual teeth to or toward an ideal centric occulsion position by simultaneously engaging, moving, and positioning said individual teeth of upper and lower teeth by force being exerted on contacting edges and a minimal area of adjacent sides of buccal and lingual surfaces of each individual tooth by the act of biting into said tooth positioner, comprising:

a one piece preform tooth impression means for providing resilient lateral force to individually move and position individual teeth of said upper and lower teeth by simultaneously engaging only the contacting edges of said upper and lower teeth and a minimal adjacent area of said buccal and lingual surface of each tooth of said upper and lower teeth, said one piece preform tooth impression means for forcing said contacting edge of each tooth to move each said tooth into the most ideal centric occulsion and cusp-fossa relationship by the act of biting into said one piece preform tooth impression means with said upper and lower teeth and for retaining said contacting edge and a minimal adjacent area of said buccal and lingual surfaces of each individual said tooth in the most ideal centric occulsion and cusp-fossa relationship by the act of biting into said one piece preform tooth impression means with said upper and lower teeth, said one piece preform tooth impression means for providing a comfortable, light prostetic device that enhances a user's cooperation for continued use, said one piece preform tooth impression means having separated resilient tooth impressions for individual teeth of said upper and lower teeth situated in certain select positions generally at the ideal centric occulsion and cusp-fossa relationship, said one piece preform tooth impression means having a top with individual upper contacting edge tooth impressions and a bottom with individual lower contacting edge tooth impressions, said upper contacting edge tooth impressions and lower contacting edge tooth impressions covering a minimal adjacent area of the buccal and lingual surface of approximately two to three millimeters of each tooth of said upper teeth and said lower teeth, said upper contacting edge tooth impression and said lower contacting edge tooth impression terminating well short of contact with gum tissue of said upper and said lower teeth.

2. An improved tooth positioner as set forth in claim 1, wherein:

said one piece preform tooth impression means is made of an elastic resilient material.

3. An improved tooth positioner as set forth in claim 1, wherein:

said upper contacting edge tooth impressions and said lower contacting edge tooth impressions are spaced apart approximately two millimeters.

* * * * *